(12) United States Patent
Janson et al.

(10) Patent No.: US 12,115,387 B2
(45) Date of Patent: Oct. 15, 2024

(54) METHOD OF GENERATING A RADIOTHERAPY TREATMENT PLAN, COMPUTER PROGRAM AND COMPUTER SYSTEM FOR GENERATING A RADIOTHERAPY TREATMENT PLAN, AND RADIOTHERAPY DELIVERY SYSTEM

(71) Applicant: RaySearch Laboratories AB (Publ), Stockholm (SE)

(72) Inventors: Martin Janson, Enskededalen (SE); Erik Traneus, Uppsala (SE)

(73) Assignee: Raysearch Laboratories AB (publ), Stockholm (SE)

( * ) Notice: Subject to any disclaimer, the term of this patent is extended or adjusted under 35 U.S.C. 154(b) by 226 days.

(21) Appl. No.: 17/906,439

(22) PCT Filed: Mar. 16, 2021

(86) PCT No.: PCT/EP2021/056603
§ 371 (c)(1),
(2) Date: Sep. 15, 2022

(87) PCT Pub. No.: WO2021/185794
PCT Pub. Date: Sep. 23, 2021

(65) Prior Publication Data
US 2023/0112426 A1    Apr. 13, 2023

(30) Foreign Application Priority Data
Mar. 18, 2020   (EP) ..................................... 20163850

(51) Int. Cl.
*A61N 5/10*   (2006.01)
(52) U.S. Cl.
CPC ......... *A61N 5/1031* (2013.01); *A61N 5/1043* (2013.01); *A61N 2005/1087* (2013.01)

(58) Field of Classification Search
CPC .. A61N 5/1071; A61N 5/1031; A61N 5/1064; A61N 1/08; A61N 5/1069;
(Continued)

(56) References Cited

U.S. PATENT DOCUMENTS

| | | | |
|---|---|---|---|
| 10,786,689 B2 * | 9/2020 | Zwart | ................. A61N 5/1071 |
| 2004/0104354 A1 | 6/2004 | Haberer et al. | |
| 2017/0281980 A1 | 10/2017 | Wulff | |

FOREIGN PATENT DOCUMENTS

| | | |
|---|---|---|
| EP | 3421085 A1 | 1/2019 |
| WO | 2019164835 A1 | 8/2019 |

OTHER PUBLICATIONS

International Search Report & Written Opinion, European Patent Office, Jun. 11, 2021, Rijswijk, Netherlands.

* cited by examiner

*Primary Examiner* — Don K Wong
(74) *Attorney, Agent, or Firm* — Noréns Patentbyrå AB

(57) ABSTRACT

A method of optimizing a radiotherapy treatment plan for delivering charged particles to a patient by pencil beam scanning, involves optimizing the treatment plan using an optimization problem that is designed to allow spots to differ in at least one of shape and orientation, and optionally also in size. This enables the optimization spots so as to cover the target in the best possible way and with a sharp penumbra along the outer edges of the target. The invention also relates to a computer program product and a computer system for use in such planning and a treatment delivery system for delivering such a plan.

14 Claims, 1 Drawing Sheet

(58) Field of Classification Search
CPC . A61N 1/00; A61N 1/02; A61N 5/103; A61N 5/1001; A61N 5/1007; A61N 5/1036; A61N 5/1039; A61N 5/1043; A61N 5/1045; A61N 5/1042; A61N 5/1047; A61N 5/1048; A61N 5/1049; A61N 5/1075; A61N 5/1077; A61N 2005/1061; A61N 2005/1062; A61N 2005/1087
See application file for complete search history.

METHOD OF GENERATING A RADIOTHERAPY TREATMENT PLAN, COMPUTER PROGRAM AND COMPUTER SYSTEM FOR GENERATING A RADIOTHERAPY TREATMENT PLAN, AND RADIOTHERAPY DELIVERY SYSTEM

TECHNICAL FIELD

The present invention relates to the planning and delivery of ion-based radiation therapy treatment.

BACKGROUND

Ion-based radiation therapy involves the use of charged particles such as protons, or ions such as helium or carbon ions. The overall goal is to deliver a dose to a target volume while minimizing unwanted dose to nearby critical organs and healthy tissue. In particular, the present invention relates to charged particle treatment using scanned focused ion beams, known as pencil beam scanning (PBS). In PBS, distinct beams are aimed at the patient in a number of discrete or quasi-discrete spots or by line scanning. A number of spots are delivered at each of a number of different energy levels, so as to cover the target in three dimensions while providing as little dose as possible outside of the target.

The region near the edges of a beam where the dosage rate decreases to a low value is known as the penumbra. There is a desire to keep the penumbra as narrow as possible.

Close to the boundary of the target, the dose fall-off should be as steep as possible towards the edges, to ensure a sufficient dose across the whole target while protecting the surrounding tissue as much as possible. The dose fall-off is governed by the lateral shape and size of the spot, with a higher fall-off for small spots. The current clinical practice when designing spots is therefore to make them small and, by tradition, as circular as technically possible given the beam transport system. Conventionally, dose planning for proton therapy aims at making the spots uniformly circular and of the same size. To achieve this, the beam is typically trimmed by means of focusing elements upstream of the patients.

Various attempts have been made to further improve the dose distribution near the edges of the target. These attempts typically involve the use of different types of static, field specific apertures. Such apertures must be manufactured specially for each patient, which is expensive and impractical. It is also possible to use dynamically adjustable collimating devices, such as a multi-leaf collimator (MLC), although this is less common for PBS systems. MLCs are also costly. Apertures also increase the production of neutron background dose during treatment, which is problematic. Any type of aperture also only affects the spots at the edges of the treatment field.

SUMMARY OF THE INVENTION

It is an object of the invention to enable the generation and delivery of particle-based radiotherapy with improved target coverage and in particular with improved characteristics near the edges of the target.

The invention relates to a computer-based method for generating a radiotherapy treatment plan for delivering charged particles to a patient by pencil beam scanning, the particles being delivered in spots, the method involving optimizing the treatment plan using an optimization problem that is designed to allow spots to differ in at least one of shape and orientation.

Thus, according to the invention, the shape and/or orientation of the spots can be varied for a particular beam energy to create spots that together will cover the target cross section for that energy, while at the same time achieving a reduction of the penumbra. This can be done per individual spot, per energy layer or per beam. One alternative organization of spot variation is to repeat energy layers or beams where the spots per energy layer (or per beam) have different shape and/or orientation. This can be set within an energy layer or beam. In preferred embodiments, the spot shapes are allowed to be circular or elliptical. In other embodiments, the spot shapes may be allowed to vary even more, to include, for example, triangular or rectangular spots, or spots having any suitable geometric shape. It should be understood that the shapes may not be geometrically perfect, due to technical limitations. For example, circular spots may not be perfectly circular. In this document, the term "circular" is taken to mean as close to circular as the delivery system is able to generate. The size of the spots may also be varied for even greater flexibility.

One or more predefined values, or combinations of values for the shape and/or orientation may be allowed. Limiting the number of possible combinations will make the delivery easier and faster. Alternatively, the shape and/or orientation may be allowed to vary freely, for maximum flexibility. This enables the spots to be positioned and oriented to cover the target in the best possible way. It also enables positioning of the edge of the spot having the best defined border so that it is aligned and oriented with respect to the target boundary to create the sharpest possible fall-off at the target boundary.

The optimization problem may be designed to allow the spots to vary in at least one portion of the target while keeping the spots uniform in a least another portion of the target. This enables maximum flexibility in the areas where this is feasible, whereas other areas can be planned in a simpler way. For example, it may be advantageous to vary the spots near the outer edges of the target while the spots farther from the edges could be kept uniform, for example uniformly circular. This will enable adaptation of the coverage to the actual shape of the target, and faster delivery of the spots in the center of the target, as well as a sharp penumbra at the outer edge of the target.

One efficient way of achieving different spot shapes and/or orientation is by means of an aperture system, such as a collimator, arranged to trim the spot fluences. Alternatively, the spots may be shaped using an electromagnetic optical focusing system. In this latter case, there will be no collimator generated neutron dose, which is particularly beneficial for pediatric applications.

A combination of an aperture device and an electromagnetic focusing system may also be used. To this end, the plan resulting from the method should include how to control the aperture device.

The greatest flexibility is achieved if the spot shaping is done per individual spot for each energy layer. Each spot can then be stretched to the optimal form, typically elliptical, and positioned and oriented in the best possible way according to the curvature of the target beam's eye view projection. Typically, the spots in the centre of the target will be kept circular since it is the spots near the boundary that will impact the penumbra around the target.

Alternatively, a limited number of spot shapes can be allowed, for example one circular spot shape, and two elliptical spot shapes having perpendicular major axes. It would also be possible to have one circular spot shape and a number of pre-defined elliptical spot shapes and sizes having pre-defined major axes. These embodiments may enable simpler planning and/or simplified and faster delivery compared to embodiments where the shape, size and/or orientation of the spots are allowed to vary freely.

Each type of spot can also be collected in a separate energy layer, so that there will be, for example, for one nominal energy, one layer with elliptical spots having a first orientation, one layer with elliptical spots having a second orientation and one layer with circular spots.

The optimization problem may also be designed to define an order of the delivery of the spots, taking the delivery time into consideration.

The invention also relates to a computer program product comprising computer-readable code means which, when run in the processor of a computer, will cause processor to perform the method according to any one of the preceding claims. The computer program product may comprise a non-transitory storage means holding the computer readable code means.

The invention also relates to a computer system comprising a processor, a data memory and a program memory arranged to hold a computer program in such a way that it can be run in the processor, the program memory comprising a computer program product according to the above.

The invention also relates to a radiotherapy treatment delivery system for delivering charged particles to a patient by PBS, the particles being delivered in spots, the system comprising a processor for controlling the delivery of treatment, the system further comprising varying means for varying at least one of the shape and orientation of the spots during delivery and the processor being arranged to control said varying. The varying means may include an electromagnetic optical system and/or a controllable aperture device arranged to vary the shape and/or orientation of the spots during delivery as discussed above. The system may also be arranged to organize the spots for the most efficient delivery.

The radiotherapy treatment delivery system according to any one of the claims may further comprise a memory, the memory holding a treatment plan and the processor being arranged to control the delivery system in accordance with the treatment plan, wherein the treatment plan has been generated using the method according to any embodiment disclosed in this application.

BRIEF DESCRIPTION OF DRAWINGS

The invention will be described in more detail in the following, by way of examples and with reference to the appended drawings.

DETAILED DESCRIPTION OF EMBODIMENTS

Figure 1:
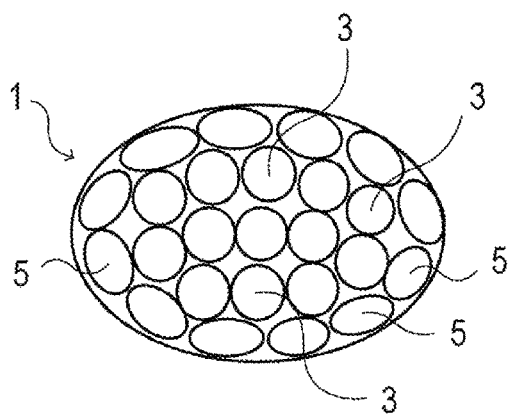
FIG. 1 illustrates schematically the spot distribution according to an embodiment of the invention.

FIG. 1 schematically discloses in beam's view an energy layer in a target 1, which is covered by spots 3, 5 according to an embodiment of the present invention. As can be seen, centrally, away from the boundaries of the target, there are substantially circular spots 3, positioned adjacent each other so that they cover the central area of the target. Near the boundaries of the target, the spots 5 are elliptical, the shape of each spot 5 being adapted to cover the area between the round spots and the boundary of the target. The spots 3,5 may be generated by any form of pencil beam scanning, including discrete scanning, quasi-discrete scanning, line scanning or by any other suitable method.

In the situation shown in FIG. 1, the shape and orientation of the spots 3, 5 are both allowed to vary freely. As mentioned above, the planning may be set up to allow only a limited set of shapes, sizes and/or orientations. For example, two elliptic shapes having perpendicular major axes, or four elliptic shapes having major axes at 45 degrees from each other may be allowed. The shape and/or orientation may be allowed to vary. The size of the spots may also be varied. For example, all spots may be the same size but different shapes and/or orientations may be allowed, or the size may be allowed to adapt, for example, to a portion of the target between another spot and the target's border.

Figure 2:
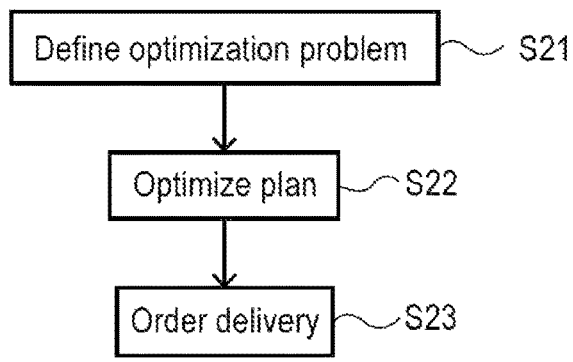
FIG. 2 is a flow chart of a treatment planning method according to the invention.

FIG. 2 illustrates an overall planning method according to the invention. in a first step S21 an optimization problem is defined. The optimization problem may be defined in any suitable way, but is set up to allow the spots to vary in at least one of shape, size or orientation. In a second step S22, the optimization is performed using the optimization problem defined in step S21. In a third, optional step S23, the energy layers included in the optimized plan are organized in such a way that the delivery will be as efficient as possible. For example, all spots having the same characteristics in terms of shape, size and orientation are delivered consecutively so that the change of spot shape only has to happen once for each set of characteristics. Alternatively, spots having the same set of characteristics may be grouped together in an energy layer so that there is one energy layer per type of spot. This organization of the spots may alternatively be performed in the delivery system.

The optimization problem may also be set up so that the spots are only allowed to vary in one or more portions of the target, while the spots in the remaining portion or portions are kept uniform. Typically, this would mean that the boundary spots, that is, spots near the targets boundary would be allowed to vary to match the outline of the target as closely as possible, whereas the spots inside these boundary spots are kept uniform, for example circular and of the same size.

Figure 3:
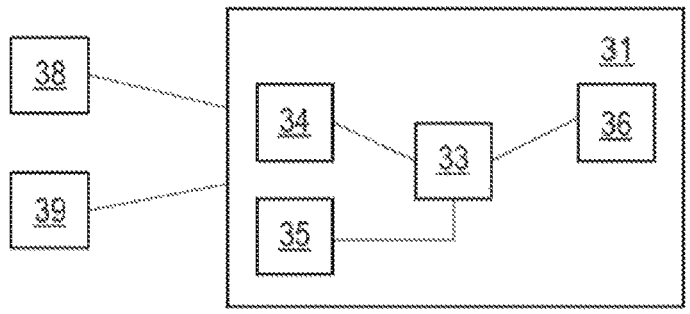
FIG. 3 discloses a computer system in which the treatment planning method of the invention can be carried out.

FIG. 3 is a schematic representation of a computer system in which the inventive treatment planning method may be performed. A computer 31 comprises a processor 33, a data memory 34 and a program memory 36. Preferably, one or more user input means 38, 39 are also present, in the form of a keyboard, a mouse, a joystick, voice recognition means or any other available user input means. The user input means may also be arranged to receive data from an external memory unit.

The data memory 34 comprises necessary data for performing the method, such as a desired dose distribution, and a segmented patient image. The program memory 36 holds a computer program arranged to make the computer perform the method steps according to some embodiment of the invention as outlined in FIG. 2.

As will be understood, the data memory 34 as well as the program memory 36 are shown and discussed schematically. There may be several data memory units, each holding one or more different types of data, or one data memory holding all data in a suitably structured way, and the same holds for the program memories. Both the program and the data can be found in one or more memories within the computer system or in another unit that is accessible from the computer system.

Figure 4:
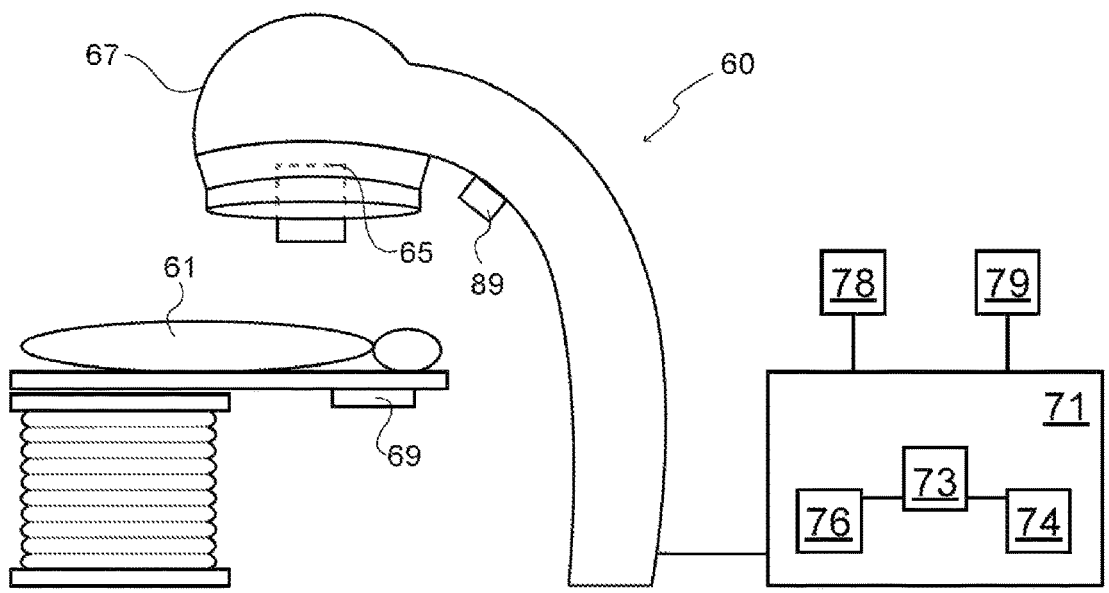
FIG. 4 discloses a treatment delivery system for delivering a treatment plan according to the invention.

FIG. 4 is an overview of a system 60 for radiotherapy treatment and/or treatment planning. As will be understood, such systems may be designed in any suitable way and the design shown in FIG. 4 is only an example. A patient 61 is positioned on a treatment couch 63. The system comprises an imaging/treatment unit having a radiation source 65 mounted in a gantry 67 for emitting radiation towards the patient positioned on the couch 63. Typically, the couch 63 and the gantry 67 are movable in several dimensions relative to each other, to provide radiation to the patient as flexibly and correctly as possible. These parts and their functions are well known to the skilled person.

A number of passive devices provided to shape the beam laterally and in depth are typically present and will not be discussed in more detail here. Means are arranged for providing radiation in the form of pencil beams. In this example the system also comprises varying means 89 for affecting the beam, for example by generating a magnetic field or an electric field or a combined magnetic/electric field that will affect the path of the particles of the beam in the beamline and means for modifying the magnetic field.

The varying means 89 is arranged to vary at least one of the shape and orientation of the spots, and optionally the spot size, during delivery. In a preferred embodiment, the varying means include an electromagnetic optical system arranged to alter the path of the charged particles so as to create spots that are different. Alternatively, or in addition to the electromagnetic system, the varying means may include an aperture shaping means in the form of a collimator or block, arranged to vary the shape and/or orientation of the spots during delivery.

The computer 71 comprises a processor 73, a data memory 74, and a program memory 76. Preferably, one or more user input means 78, 79 are also present, in the form of a keyboard, a mouse, a joystick, voice recognition means or any other available user input means. The user input means may also be arranged to receive data from an external memory unit.

The data memory 74 may comprise clinical data and/or other information used to obtain a treatment plan. Typically, the data memory 74 comprises one or more patient images to be used in treatment planning according to embodiments of the invention. The program memory 76 holds at least one computer program arranged to cause the processor to control the delivery system according to the result of the optimization. If the organization of spots for delivery is not performed by the planning system as shown in step S23, the processor 73 may also perform this step, that is, determining a suitable order for the delivery of the spots to minimize the delivery time.

As will be understood, the data memory 74 and the program memory 76 are shown and discussed only schematically. There may be several data memory units, each holding one or more different types of data, or one data memory holding all data in a suitably structured way, and the same holds for the program memories. One or more memories may also be stored on other computers. The computer may also be arranged to perform the optimization.

Although the variations in spot shape and orientation have been exemplified above for circular and/or elliptical spots, it should be understood that the spots can be given any suitable shape by means of aperture devices designed for different shapes, including triangular, rectangular, or any other geometric shape that may help cover a particular target in the best possible way.

The invention claimed is:

1. A computer-based method for generating a radiotherapy treatment plan for delivering charged particles to a target in a patient by pencil beam scanning, the particles being delivered in spots, the method involving optimizing the treatment plan using an optimization problem, wherein the optimization problem is designed to allow spots to differ in at least one of shape and orientation.

2. The method of claim 1, wherein the optimization problem is designed to allow two or more predefined sets of values for shape and/or orientation for the spots.

3. The method of claim 1, wherein the optimization problem is designed to allow the spots to vary freely in at least one of shape and orientation.

4. The method of claim 1, wherein the optimization problem is designed to allow the spots to vary in at least one portion of the target while keeping the spots uniform in at least another portion of the target.

5. The method of claim 4, wherein the optimization problem is designed to allow the spots near the target boundary to vary while keeping the spots in the center of the target uniform.

6. The method of claim 1, further comprising the step of defining an order of the delivery of the spots considering the delivery time.

7. The method of claim 1, wherein the treatment plan is arranged to of control an aperture device to define the spot shape and/or the orientation of the spot's shape.

8. The method of claim 1, wherein the optimization problem is also arranged to allow the spots to vary in size.

9. A computer program product comprising a non-transitory computer readable storage medium having program instructions embodied which, when run in a processor of a computer, will cause the processor to perform the method of claim 1.

10. A computer system comprising a processor, a data memory and a program memory arranged to hold a computer program in such a way that it can be run in the processor, wherein the program memory comprises a computer program product according to claim 9.

11. A radiotherapy treatment delivery system for delivering charged particles to a patient by PBS, the particles being delivered in spots, the system comprising a processor for controlling the delivery of treatment, characterized in that it comprises varying means for varying at least one of the shape and orientation of the spots during delivery and that the processor is arranged to control said varying.

12. The radiotherapy treatment delivery system of claim 11, wherein the varying means include an electromagnetic optical system.

13. The radiotherapy treatment delivery system of claim 11, wherein the varying means include a controllable aperture device arranged to vary the shape and/or orientation of the spots during delivery.

14. The radiotherapy treatment delivery system of claim 10, further comprising a memory, the memory holding a treatment plan and the processor being arranged to control the delivery system in accordance with the treatment plan, wherein the treatment plan has been generated using the method according to any one of the claims 1-8.

* * * * *